United States Patent
Blann et al.

(10) Patent No.: US 12,344,577 B2
(45) Date of Patent: *Jul. 1, 2025

(54) METHODS FOR DEHYDROGENATING HYDROCARBONS

(71) Applicant: Dow Global Technologies LLC, Midland, MI (US)

(72) Inventors: Kevin Blann, Lake Jackson, TX (US); Alexey Kirilin, Hoek (NL); Andrzej Malek, Midland, MI (US); Victor Sussman, Midland, MI (US); Matthew T. Pretz, Freeport, TX (US); Brien A. Stears, League City, TX (US); Barry B. Fish, Lake Jackson, TX (US); Eric E. Stangland, Midland, MI (US); Brian W. Goodfellow, Sugarland, TX (US); Manish Sharma, Missouri City, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,619

(22) Filed: Apr. 26, 2023

(65) Prior Publication Data

US 2023/0257327 A1    Aug. 17, 2023

Related U.S. Application Data

(63) Continuation of application No. 17/271,139, filed as application No. PCT/US2019/048391 on Aug. 27, 2019, now Pat. No. 11,724,974.

(Continued)

(51) Int. Cl.
   *C07C 5/48* (2006.01)
   *B01J 21/04* (2006.01)
   (Continued)

(52) U.S. Cl.
   CPC .............. *C07C 5/48* (2013.01); *B01J 21/04* (2013.01); *B01J 21/06* (2013.01); *B01J 21/10* (2013.01);
   (Continued)

(58) Field of Classification Search
   CPC ....... C07C 5/3335; C07C 5/3337; C07C 5/48; C07C 2521/04; C07C 2521/06;
   (Continued)

(56) References Cited

U.S. PATENT DOCUMENTS 4,806,624 A   2/1989 Herber et al.
4,827,066 A   5/1989 Herber et al.
(Continued)

FOREIGN PATENT DOCUMENTS

CN     86104653 A   4/1987
CN     1172790 A    2/1998
(Continued)

OTHER PUBLICATIONS

Geldart, D., "Types of Gas Fluidization," Powder Technology, 1973, 7, 285-292.

(Continued)

*Primary Examiner* — In Suk C Bullock
*Assistant Examiner* — Jason Y Chong
(74) *Attorney, Agent, or Firm* — Dinsmore & Shohl LLP

(57) ABSTRACT

According to one or more embodiments described herein, a method for dehydrogenating hydrocarbons may include passing a hydrocarbon feed comprising one or more alkanes or alkyl aromatics into a fluidized bed reactor, contacting the hydrocarbon feed with a dehydrogenation catalyst in the fluidized bed reactor to produce a dehydrogenated product and hydrogen, and contacting the hydrogen with an oxygen-rich oxygen carrier material in the fluidized bed reactor to combust the hydrogen and form an oxygen-diminished (Continued)

oxygen carrier material. In additional embodiments, a dual-purpose material may be utilized which has dehydrogenation catalyst and oxygen carrying functionality.

19 Claims, 4 Drawing Sheets

Related U.S. Application Data

(60) Provisional application No. 62/814,045, filed on Mar. 5, 2019, provisional application No. 62/725,497, filed on Aug. 31, 2018.

(51) Int. Cl.
*B01J 21/06* (2006.01)
*B01J 21/10* (2006.01)
*B01J 23/08* (2006.01)
*B01J 23/26* (2006.01)
*B01J 23/42* (2006.01)
*C07C 5/333* (2006.01)

(52) U.S. Cl.
CPC .............. *B01J 23/08* (2013.01); *B01J 23/26* (2013.01); *B01J 23/42* (2013.01); *C07C 2521/04* (2013.01); *C07C 2521/06* (2013.01); *C07C 2521/10* (2013.01); *C07C 2523/08* (2013.01); *C07C 2523/26* (2013.01); *C07C 2523/42* (2013.01)

(58) Field of Classification Search
CPC ............ C07C 2521/10; C07C 2523/04; C07C 2523/08; C07C 2523/14; C07C 2523/26; C07C 2523/42; C07C 2523/62; C07C 5/333; C07C 11/04; B01J 21/04; B01J 21/06; B01J 21/10; B01J 23/08; B01J 23/26; B01J 23/42; Y02E 20/34; F23C 2900/99008
See application file for complete search history.

(56) References Cited

U.S. PATENT DOCUMENTS

| | | | |
|---|---|---|---|
| 5,430,209 | A | 7/1995 | Agaskar et al. |
| 5,430,210 | A | 7/1995 | Grasselli et al. |
| 5,527,979 | A | 6/1996 | Agaskar et al. |
| 5,563,314 | A | 10/1996 | Agaskar et al. |
| 6,525,232 | B1 | 2/2003 | Bierl et al. |
| 6,576,804 | B1 | 6/2003 | Heineke et al. |
| 7,122,492 | B2 | 10/2006 | Ou et al. |
| 7,122,493 | B2 | 10/2006 | Ou et al. |
| 7,122,494 | B2 | 10/2006 | Ou et al. |
| 7,122,495 | B2 | 10/2006 | Ou et al. |
| 7,125,817 | B2 | 10/2006 | Ou et al. |
| 8,669,406 | B2 | 3/2014 | Pretz et al. |
| 9,370,759 | B2 | 6/2016 | Pretz et al. |
| 2004/0010174 | A1 | 1/2004 | Wang et al. |
| 2005/0177016 | A1 | 8/2005 | Sanfilippo et al. |
| 2009/0292153 | A1 | 11/2009 | Cai et al. |
| 2016/0318828 | A1 | 11/2016 | Washburn et al. |
| 2017/0313637 | A1 | 11/2017 | Sofranko et al. |
| 2017/0354955 | A1 | 12/2017 | Hossain et al. |

FOREIGN PATENT DOCUMENTS

| | | |
|---|---|---|
| CN | 107428633 A | 12/2017 |
| EP | 2208410 A1 | 4/1986 |
| EP | 0330304 A1 | 1/1989 |
| EP | 482276 A1 | 4/1992 |
| WO | 8504821 A1 | 11/1985 |
| WO | 2005077867 A2 | 8/2005 |
| WO | 2006036193 A1 | 4/2006 |
| WO | 2010133565 A1 | 11/2010 |
| WO | 2016049144 A1 | 3/2016 |
| WO | 2016160273 A1 | 10/2016 |
| WO | 2016209811 A1 | 12/2016 |
| WO | 2017144584 A1 | 8/2017 |
| WO | 2018005456 A1 | 1/2018 |
| WO | 2018025117 A1 | 2/2018 |
| WO | 2018049389 A1 | 3/2018 |
| WO | 2018232133 A1 | 12/2018 |

OTHER PUBLICATIONS

Geldart, D., "Gas Fluidization Technology", John Wiley & Sons (New York, 1986), 38-48.
Cavani et al., "Alternative Processes for the Production of Styrene", Applied Catalysis A: General, 1995, 219-239.
Shafiefarhood et al., "Fe2O3@LaxSr1-xFeO3 Core-shell redox Catalyst for Methane Partial Oxidation", Chemcatchem, 2014, 790-799.
Yusuf et al., "Effect of Promoters on Manganese-Containing Mixed Metal Oxides for Ocidative Dehydrogenation of Ethane via a Cyclic Redox Scheme", ACS Catalysis, 2017, 5163-5173.
International Search Report and Written Opinion pertaining to PCT/US2019/048391, dated Dec. 11, 2019.
Yusuf et al., "Effects of Sodium and Tungsten Promoters on Mg6MnO8-Based Core-shell Redox Catalysts for Chemical Looping-Oxidative Dehydrogenation of Ethane", ACS Catalysis, 2019, 3174-3186.
Xu et al., "Self-assembly Template Combustion Synthesis of a Core-shell CuO@TiO2-Al2O3 Hierarchical Structure as an Oxygen Carrier for the Chemical-lopping Processes", Combustion and Flame, 2015, 3030-3045.
Neal et al., "Oxidative Dehydrogenation of Ethane: a Chemical Looping Approach", Energy Technology, 2016, 4, 1200-1208.
Notice of Allowance pertaining to U.S. Appl. No. 17/271,139 dated Mar. 22, 2023.
Chinese Office Action dated May 23, 2023, pertaining to Chinese Patent Application No. 201980058633.9 18 pages.
Chinese Search Report dated May 23, 2023, pertaining to Chinese Patent Application No. 201980058633.9 3 pages.
Fluidization Engineering Principles cited as "Common Knowledge Document", Tsinghua University Press, Nov. 3, 2013, 4 pages.
Brazilian Office Action dated Jun. 2, 2023, pertaining to Brazilian Patent Application No. BR112021003382-3, 8 pages.
Chinese Office Action dated Oct. 20, 2023, pertaining to CN Patent Application No. 201980058633.9, 12 pgs.
Brazilian Office Action dated Jun. 13, 2024, pertaining to BR Patent Application No. BR112021003382.3, 14 pgs.
Communication pursuant to Article 94(3) EPC dated Mar. 18, 2025, pertaining to EP Patent Application No. 19765923.8, 7 pgs.
Beckers et al. "Sustainable selective oxidations using ceria-based materials", Green Chem., 2010, 12, 939-948.

METHODS FOR DEHYDROGENATING HYDROCARBONS

CROSS-REFERENCES TO RELATED APPLICATIONS

This Application is a continuation application of U.S. patent application Ser. No. 17/271,139 filed on Feb. 24, 2021, which is a National Stage Entry under 35 U.S.C. § 371 of International Patent Application No. PCT/US2019/048391, filed Aug. 27, 2019, which claims priority to U.S. App. No. 62/725,497, entitled "METHODS FOR DEHYDROGENATING HYDROCARBONS," filed on, Aug. 31, 2018, and U.S. App. No. 62/814,045, entitled "METHODS FOR DEHYDROGENATING HYDROCARBONS," filed on Mar. 5, 2019, the entire disclosures of which are hereby incorporated by reference.

TECHNICAL FIELD

Embodiments described herein generally relate to chemical processing and, more specifically, to processes and systems utilized for catalytic dehydrogenation.

BACKGROUND

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

SUMMARY

There is a continued need for processes and apparatuses that are suitable for producing light olefins from hydrocarbon feed streams. One method for producing light olefins may be through a dehydrogenation reaction. One example of a catalytic dehydrogenation process used to produce light olefins may include utilizing catalysts such as, but not limited to, gallium, platinum, or chromium-including catalysts to react a feed stream comprising one or more alkanes, such as ethane, propane, n-butane, and/or i-butane or alkyl aromatics such as ethylbenzene. Such a reaction scheme is shown in Chemical Formula 1:

$$C_2H_6 \leftrightarrow C_2H_4 + H_2 \quad \Delta H_0 = +137 \text{ kJ/mol} \quad (1)$$

The dehydrogenation reaction may be promoted by reducing or removing hydrogen, which pushes the reaction equilibrium toward the products. That is, in Chemical Formula 1, the removal of hydrogen pushes the equilibrium to the right, which thereby may allow the reaction to achieve increased levels of conversion or operate at higher reactor pressures.

The disclosed processes for the production of light olefins may incorporate dehydrogenation and hydrogen combustion. Due to the removal of hydrogen, the disclosed processes may operate at higher pressures and lower temperatures relative to the conventional processes yet achieve comparable conversion levels. As a result, the disclosed processes that incorporate hydrogen combustion may allow for relatively smaller process units and therefore reduce capital cost. It has been found that the incorporation of an oxygen carrier material in a dehydrogenation reaction may reduce needed input heat and/or may reduce subsequent unreacted alkane, alkyl aromatic, and hydrogen separation costs. As described herein, the incorporation of an oxygen carrier material, sometimes mixed with the dehydrogenation catalyst and recycled through the process, may promote the combustion of hydrogen to form water.

On the other hand, conventional processes for producing light olefins may require high reaction temperatures. For example some conventional processes may require reactor temperatures above 850° C. The high temperatures may cause conventional processes to be expensive. For example, because of the higher temperatures required by these conventional processes, the reactors utilized in such processes may not have the ability to incorporate reactor internals or other design features. Alternatively, such processes may require reactor internals and other process units to be made from specialty materials, which increase capital costs.

It is contemplated that in some embodiments, pushing the equilibrium to the right in the disclosed processes may simultaneously reduce the downstream separation costs. For example, in downstream processes, the product stream may require liquefaction. As such, the reduction of hydrogen in the product stream may reduce the volume of gas that would need to be liquefied or change the required temperature for liquefying the hydrocarbons due to lower hydrogen content. Therefore, the complete or partial removal of hydrogen in in the product stream may reduce the energy requirements for downstream liquefaction processes. In addition, the complete or partial removal of hydrogen in in the product stream may subsequently reduce other downstream separation costs by eliminating the need for other process units that may be utilized to separate out the hydrogen from the product stream (prior to or after liquefaction).

The production of light olefins by conventional dehydrogenation processes (e.g., those that do not incorporate hydrogen combustion) may be relatively expensive due to the high heat loads needed for the endothermic dehydrogenation reaction and/or the downstream separation steps sometimes needed to separate the unreacted alkane or alkyl aromatic and remove hydrogen that is produced in the dehydrogenation reaction. Regarding reduced heat input, catalytic dehydrogenation processes are generally endothermic and require heat. However, the exothermic combustion of hydrogen can somewhat counterbalance that heat input requirement. Additionally, the oxygen carrier material, once diminished in oxygen content following the combustion, may be regenerated to regain its oxygen, which may be exothermic. This exothermic regeneration step may further counterbalance the heat input requirement to maintain the dehydrogenation reaction. In some embodiments, the heat produced by the oxygen carrier regeneration and combustion reaction may completely cover the heat needed for the endothermic dehydrogenation reaction and other heat demands such as heating the feed gases (air, hydrocarbon, etc.) or balancing heat losses, or at least reduce any supplemental fuel needs of the system.

In additional embodiments, the use of an oxygen carrier material that is selective for hydrogen combustion may be utilized. Such an oxygen carrier material may be selective for combusting hydrogen as opposed to reactant or hydrocarbons.

It should be understood that in some embodiments described herein, separate dehydrogenation catalysts and oxygen carrier materials are utilized, sometimes in the same reaction vessel. For example, in the same reaction vessel, a dehydrogenation catalyst may form the dehydrogenation product and hydrogen, and a separate oxygen carrier material may combust the hydrogen. However, in additional embodiments, the dehydrogenation catalyst and the oxygen carrier material functionality may be combined into a single material, referred to herein as a "dual purpose material" which is either oxygen rich or oxygen poor. Such a dual purpose material may be substituted into several of the applicable embodiments disclosed herein for the oxygen carrier material and dehydrogenation catalyst. For example, the discussed dual purpose material may be functional as an oxygen carrier and as a dehydrogenation catalyst.

According to at least one embodiment of the present disclosure, a method for dehydrogenating hydrocarbons may include passing a hydrocarbon feed comprising one or more alkanes or alkyl aromatics into a fluidized bed reactor, contacting the hydrocarbon feed with a dehydrogenation catalyst in the fluidized bed reactor to produce a dehydrogenated product and hydrogen, contacting the hydrogen with an oxygen-rich oxygen carrier material in the fluidized bed reactor to combust the hydrogen and form an oxygen-diminished oxygen carrier material, passing the oxygen-diminished oxygen carrier material and the dehydrogenation catalyst to a regeneration unit, oxidizing the oxygen-diminished oxygen carrier material in the regeneration unit to form the oxygen-rich oxygen carrier material, and passing the oxygen-rich oxygen carrier material to the fluidized bed reactor. At least 95 wt. % of the hydrocarbon feed may have an atmospheric boiling point of less than or equal to 300° C. The oxygen-rich oxygen carrier material may be reducible.

According to another embodiment of the present disclosure, a method for dehydrogenating hydrocarbons may include passing a hydrocarbon feed comprising one or more alkanes or alkyl aromatics into a first fluidized bed reactor, contacting the hydrocarbon feed with a dehydrogenation catalyst in the first fluidized bed reactor to produce a dehydrogenation effluent comprising dehydrogenated product and hydrogen; passing the dehydrogenation effluent to a second fluidized bed reactor, contacting the hydrogen of the dehydrogenation effluent with an oxygen-rich oxygen carrier material in the second fluidized bed reactor to combust at least a portion of the hydrogen and form an oxygen-diminished oxygen carrier material, passing the oxygen-diminished oxygen carrier material to a first regeneration unit, oxidizing the oxygen-diminished oxygen carrier material in the first regeneration unit to form the oxygen-rich oxygen carrier material, and passing the oxygen-rich oxygen carrier material from the first regeneration unit to the second reactor. At least 95 wt. % of the hydrocarbon feed may have an atmospheric boiling point of less than or equal to 300° C. The oxygen-rich oxygen carrier material may be reducible.

According to another embodiment of the present disclosure, a method for dehydrogenating hydrocarbons may include passing a hydrocarbon feed comprising one or more alkanes or alkyl aromatics into a fluidized bed reactor and contacting the hydrocarbon feed with an oxygen-rich dual-purpose material in the fluidized bed reactor to produce a dehydrogenated product. The oxygen-rich dual-purpose material is reducible. Released hydrogen from the hydrocarbon feed may be reacted with released oxygen from the oxygen-rich dual-purpose material. Contacting hydrogen with the oxygen-rich dual-purpose material in the fluidized bed reactor may combust the hydrogen and form an oxygen-diminished dual-purpose material. The method for dehydrogenating hydrocarbons may include passing the oxygen-diminished dual-purpose material to a regeneration unit, oxidizing the oxygen-diminished dual-purpose material in the regeneration unit to form the oxygen-rich dual-purpose material, and passing the oxygen-rich dual-purpose material to the fluidized bed reactor. At least 95 wt. % of the hydrocarbon feed may have an atmospheric boiling point of less than or equal to 300° C.

These and other embodiments are described in more detail in the following Detailed Description in conjunction with the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
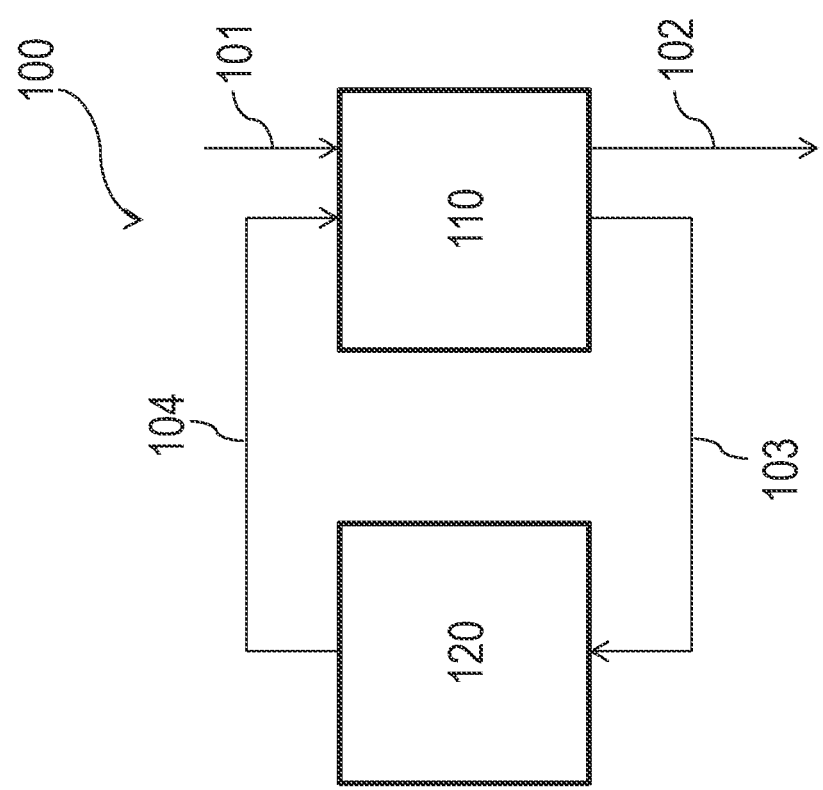
FIG. 1 schematically depicts a catalytic dehydrogenation system, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Specific embodiments of the present application will now be described. The disclosure may, however, be embodied in different forms and should not be construed as limited to the embodiments set forth in this disclosure. Rather, these embodiments are provided so that this disclosure will fully convey the scope of the subject matter to those skilled in the art.

Embodiments related to methods for processing chemical streams to form light olefins are disclosed herein. In various embodiments, processes may include a dehydrogenation catalyst and an oxygen carrier material and may catalytically dehydrogenate an alkane or alkyl aromatic and combust hydrogen with the oxygen carrier material as described herein. In additional embodiments, processes may include a "dual-purpose material" that may catalytically dehydrogenate an alkane or alkyl aromatic, as well as combust hydrogen with oxygen. As such, the dual-purpose material may act as both a dehydrogenation catalyst as well as oxygen carrier material. It should be understood that, in at least the embodiments described herein where an oxygen carrier material and a dehydrogenation catalyst are utilized in the same reaction vessel (such as those of FIG. 1), such a dual-purpose material may be utilized either in replacement or in combination with the oxygen carrier material and the dehydrogenation catalyst. Unless specified herein, an "oxygen carrier material" may generally refer to an oxygen-rich oxygen carrier material or an oxygen-deficient oxygen carrier material. Unless specified herein, the "dual-purpose material" may generally refer to an oxygen-rich dual-purpose material or an oxygen-deficient dual-purpose material. For example, an oxygen-deficient state may be present after some oxygen is utilized for combustion and may be oxygen-rich prior to the combustion, following regeneration of the oxygen-deficient state material. The reactions may take place in one or more fluidized bed reactors, such as circulating fluidized bed reactors. The reactors may be, for example, risers or downers.

It should be understood that in some embodiments, separate particles constitute the dehydrogenation catalyst and the oxygen carrier material. One contemplated advantage of such a system is that by adding, removing, or substituting one or both of the dehydrogenation catalyst and oxygen carrier material, the functionality of the system can be altered, even when the system is on-line. For example, the reaction heat load could be adjusted by adding or removing one or both of the dehydrogenation catalyst and the oxygen carrier material. This may be advantageous, in some embodiments, as compared with a dual purpose material, since the dual purpose particle's heat balance must be determined prior to reaction and cannot be easily adjusted by varying the amount of dehydrogenation catalyst versus oxygen carrier material. Control of the ratio of dehydrogenation catalyst versus oxygen carrier material may further be advantageous since reaction selectivity may be better tuned. For example, the amount of hydrogen in the system may be used to control the degree of combustion, or component balances may be used to optimize downstream separation processes.

Now referring to FIG. 1, a reactor system 100 is depicted that may be used to perform the methods of the present disclosure. The reactor system 100 may include a fluidized bed reactor 110 and a regeneration unit 120. A hydrocarbon feed 101 may be passed into a fluidized bed reactor 110. In one or more embodiments, the hydrocarbon feed 101 may comprise one or more alkanes or alkyl aromatics. The hydrocarbon feed 101 may comprise one or more of ethane, propane, butane, or ethylbenzene. According to one or more embodiments, the hydrocarbon feed 101 may comprise at least 50 wt. %, at least 60 wt. %, at least 70 wt. %, at least 80 wt. %, at least 90 wt. %, at least 95 wt. % or even at least 99 wt. % of ethane. In additional embodiments, the hydrocarbon feed 101 may comprise at least 50 wt. %, at least 60 wt. %, at least 70 wt. %, at least 80 wt. %, at least 90 wt. %, at least 95 wt. % or even at least 99 wt. % of propane. In additional embodiments, the hydrocarbon feed 101 may comprise at least 50 wt. %, at least 60 wt. %, at least 70 wt. %, at least 80 wt. %, at least 90 wt. %, at least 95 wt. % or even at least 99 wt. % of butane. In additional embodiments, the hydrocarbon feed 101 may comprise at least 50 wt. %, at least 60 wt. %, at least 70 wt. %, at least 80 wt. %, at least 90 wt. %, at least 95 wt. % or even at least 99 wt. % of ethylbenzene. In additional embodiments, the hydrocarbon feed 101 may comprise at least 50 wt. %, at least 60 wt. %, at least 70 wt. %, at least 80 wt. %, at least 90 wt. %, at least 95 wt. % or even at least 99 wt. % of the sum of ethane, propane, butane and ethylbenzene.

According to one or more embodiments, at least 95 wt. % of the hydrocarbon feed 101 may have an atmospheric boiling point of less than or equal to 300° C. According to additional embodiments, at least 95 wt. % of the hydrocarbon feed 101 may have an atmospheric boiling point of less than or equal to 275° C., less than or equal to 250° C., less than or equal to 225° C., less than or equal to 200° C., less than or equal to 175° C., less than or equal to 150° C., less than or equal to 125° C., or even less than or equal to 100° C. For example, the hydrocarbon feed 101 may not be a crude oil.

In some embodiments, reactor system 100 may include a circulating fluidized bed (CFB) dehydrogenation process. The CFB dehydrogenation process may include a fluidized bed reactor 110 and a regeneration unit 120, both fluid bed based. The fluidized bed reactor 110 may, in some embodiments, include a downstream reactor section, an upstream reactor section, and a catalyst separation section, which serves to separate the dehydrogenation catalyst from the chemical products formed in the fluidized bed reactor 110.

According to additional embodiments, the reactor may operate with a "back-mixed" fashion where the feed hydrocarbons enter the reactor, as to closely approximate isothermal conditions. As such, the fluid velocity at this region may be low enough and the catalyst flux may be great enough such that a dense bed may form at or around where the hydrocarbons are injected. In some embodiments, the superficial velocity of the reactor may be from 3-80 ft/s, such as from 3-40 ft/s, or 10-30 ft/s. The catalyst flux in the reactor may be from 1-300 lb/ft$^2$-s, such as from 40-200 lb/ft$^2$-s, or from 60-160 lb/ft$^2$-s. The reactor may include multiple diameters, and may include one or more frustums to increase or decrease catalyst and/or gaseous reactant velocity. The reactor may operate with a gas residence time of from 0.1-10 seconds, such as from 0.5-6 seconds.

An embodiment of the general operation of a fluidized bed reactor 110 to conduct a continuous reaction will now be described. As used herein, the "solids" in the fluidized bed reactor 110 may include the dehydrogenation catalyst, the oxygen carrier material, and/or a dual-purpose material. In some embodiments, the fluidized bed reactor may include from 1 wt. % to 99 wt. %, such as from 5 wt. % to 95 wt. %, or from 25 wt. % to 75 wt. %, dehydrogenation catalyst based on the total weight of the solids in the fluidized bed reactor. In other embodiments, the fluidized bed reactor may include from 25 wt. % to 50 wt. % dehydrogenation catalyst based on the total weight of the solids in the fluidized bed reactor. In some embodiments, the fluidized bed reactor may include from 1 wt. % to 99 wt. %, such as from 5 wt. % to 95 wt. %, or from 75 wt. % to 25 wt. %, oxygen carrier material based on the total weight of the solids in the fluidized bed reactor. In other embodiments, the fluidized bed reactor may include from 50 wt. % to 75 wt. % oxygen carrier material on the total weight of the solids in the fluidized bed reactor. In some embodiments relatively large amounts of oxygen carrier material may be present (e.g., at least 80 wt. %, at least 85 wt. %, or even at least 90 wt. %), particularly if there is relatively slow release of oxygen by the oxygen carrier materials as compared the rate of dehydrogenation. In some embodiments, the fluidized bed reactor may include up to 95 wt. %, 99 wt. %, or even 100 wt. % of dual-purpose material of the total weight of the solids in the fluidized bed reactor. For example all or a far majority of the solids may be dual-purpose material when utilized.

During operation of the fluidized bed reactor 110 of the reactor system 100, the hydrocarbon feed 101 may enter a riser within the fluidized bed reactor 110, and the product stream may exit the reactor system 100 via stream 102. According to one or more embodiments, the reactor system 100 may be operated by feeding a chemical feed (e.g., in a feed stream such as hydrocarbon feed 101) into the fluidized bed reactor.

According to one or more embodiments, a fluidized dehydrogenation catalyst may be fed into the fluidized bed reactor 110. In some embodiments, an oxygen-rich oxygen carrier material may also be fed into the fluidized bed reactor 110. The chemical feed may contact one or more of the dehydrogenation catalyst, the oxygen-rich oxygen carrier material, or both in the fluidized bed reactor 110. Each of the chemical feed, the dehydrogenation catalyst, and the oxygen-rich oxygen carrier material, may flow upwardly into and through the fluidized bed reactor 110 to produce a chemical product and an oxygen-diminished oxygen carrier material. The contacting of the dehydrogenation catalyst with the hydrocarbon feed may produce a dehydrogenated product and hydrogen. Additionally, within the fluidized bed reactor 110, the hydrogen may be contacted with the oxygen-rich oxygen carrier material in the fluidized bed reactor. The oxygen-rich oxygen carrier material may be reducible. The contacting of the oxygen-rich oxygen carrier material with the hydrogen may combust the hydrogen and form an oxygen-diminished oxygen carrier material.

In some embodiments, the chemical product, the dehydrogenation catalyst, and the oxygen-diminished oxygen carrier material may be passed to a separation device in a separation section within the fluidized bed reactor 110. The dehydrogenation catalyst, the oxygen-diminished oxygen carrier material, or both may be separated from the chemical product in the separation device within the fluidized bed reactor 110. The chemical product may then be transported out of the separation section of the fluidized bed reactor 110. For example, the separated vapors may be removed from the fluidized bed reactor 110 via a pipe at a gas outlet port of the separation section within the fluidized bed reactor 110. According to one or more embodiments, the separation device may be a cyclonic separation system. The cyclonic separation system may include two or more stages of cyclonic separation.

In one or more embodiments, the fluidized bed reactor 110 may operate with a residence time of the vapor in the fluidized bed reactor of less than 10 seconds (such less than 9 seconds, less than 8 seconds, less than 7 seconds, less than 6 seconds, less than 5 seconds, less than 4 seconds, or even less than 3 seconds.

In one or more embodiments, the fluidized bed reactor 110 may operate at a temperature of greater than 600° C. and less than or equal to 800° C. In some embodiments, the temperature in the fluidized bed reactor 110 may be from 625° C. or 650° C. to 770° C. In other embodiments, the temperature in the fluidized bed reactor 110 may be from 700° C. to 750° C. Without being bound by any particular theory, it is believed that too low of temperature (e.g., 600° C. or less) may limit the maximum conversion of the hydrocarbon due to equilibrium constraints as well as lowers the rate of dehydrogenation by the thermal and catalytic component. Too low of temperatures may also result in a slow rate of oxygen release from the oxygen-carrier material and low hydrogen combustion. On the other hand, high temperatures (e.g., greater than 800° C.) may result in thermal degradation of the products produced and may result in a lower product selectivity than is economically feasible. In some embodiments, the primary feed component(s) may be propane, ethylbenzene, and/or butane, and the fluidized bed reactor 110 may operate at a temperature of greater than 600° C. In additional embodiments, the primary feed component may be ethane, and the fluidized bed reactor 110 may operate at a temperature of at least 625° C.

In some embodiments, the fluidized bed reactor 110 may operate at a pressure of at least atmospheric pressure (about 14.7 psia). In some embodiments, the fluidized bed reactor 110 may operate at a pressure of about 500 psia. In other embodiments, the fluidized bed reactor 110 may operate at a pressure from about 4 psia to about 160 psia, from about 20 psia to about 100 psia, or from about 30 psia to about 60 psia. In some embodiments, the regeneration unit 120 may operate with a pressure of within 30 psi of the fluidized bed reactor 110.

In some embodiments, the hydrocarbon feed may contact the dehydrogenation catalyst, the oxygen-rich oxygen carrier material, or both in an upstream reactor section of the fluidized bed reactor 110. Each of the chemical feed, the dehydrogenation catalyst, and the oxygen-rich oxygen carrier material, may flow upwardly into and through the downstream reactor section of the fluidized bed reactor 110 to produce a chemical product and an oxygen-diminished oxygen carrier material. In one or more embodiments, a feed distributor within the fluidized bed reactor 110 may be operable to dispense the hydrocarbon feed stream at all shroud distributor velocities from 200 ft/s to 50 ft/s. In such embodiments, various feed streams may be utilized while maintaining the desired reactor characteristics, such as operating as a fast fluidized, turbulent, or bubbling bed reactor in the upstream reactor section of the fluidized bed reactor 110 and as a dilute phase riser reactor in the downstream reactor section of the fluidized bed reactor 110. For example, suitable distributors are disclosed in U.S. Pat. No. 9,370,759, the teachings of which are incorporated herein by reference in their entirety. The chemical product, the dehydrogenation catalyst, and the oxygen-diminished oxygen carrier material may be passed out of the downstream reactor section of the fluidized bed reactor 110 to the separation device within the fluidized bed reactor 110, where the dehydrogenation catalyst, the oxygen-diminished oxygen carrier material, or both may be separated from the chemical product.

In additional embodiments, the weight hourly space velocity (WHSV) for the disclosed processes may range from 0.1 pound (lb) to 100 lb of chemical feed per hour (h) per lb of solids in the reactor (lb feed/h/lb solids). In some embodiments, where the fluidized bed reactor 110 comprises an upstream reactor section that operates as a fast fluidized, turbulent, or bubbling bed reactor and a downstream reactor section that operates as a dilute phase riser reactor, the superficial gas velocity may range therein from 2 ft/s (about 0.61 m/s) to 10 ft/s (about 3.05 m/s) in the upstream reactor section, and from 30 ft/s (about 9.14 m/s) to 70 ft/s (about 21.31 m/s) in the downstream reactor section. In additional embodiments, a reactor configuration that is fully of a riser-type may operate at a single high superficial gas velocity, for example, in some embodiments at least 30 ft/s (about 9.15 m/s) throughout.

The residence time of the solids in the fluidized bed reactor 110 may typically vary from 0.5 seconds (sec) to 240 sec. In other embodiments, the residence time of the solids may be from about 0.5 sec to about 200 sec, from about 0.5 sec to about 100 sec, from about 0.5 sec to about 50 sec, or about 0.5 sec to about 20 sec.

In additional embodiments, the ratio of the solids to the hydrocarbon feed 101 in the fluidized bed reactor 110 may range from 5 to 150 on a weight to weight (w/w) basis. In some embodiments, the ratio may range from 10 to 40, such as from 12 to 36, or from 12 to 24.

In additional embodiments, the flux of the solids (the dehydrogenation catalyst and the oxygen carrier material) may be from 1 pound per square foot-second (lb/ft$^2$-s) (about 4.89 kg/m2-s) to 300 lb/ft$^2$-s (to about 97.7 kg/m2-s), such as from 1-20 lb/ft$^2$-s, in the upstream reactor section, and from 1 lb/ft$^2$-s (about 48.9 kg/m2-s) to 300 lb/ft$^2$-s (about 489 kg/m2-s), such as from 10-100 lb/ft$^2$-s, in the downstream reactor section.

In one or more embodiments, the dehydrogenation catalyst may include solid particulate catalyst types that are capable of fluidization. In some embodiments, the dehydrogenation catalyst may exhibit properties known in the industry as "Geldart A" properties. Catalyst type may be classified as "Group A" or "Group B" according to D. Geldart, Gas Fluidization Technology, John Wiley & Sons (New York, 1986), 34-37; and D. Geldart, "Types of Gas Fluidization," Powder Technol. 7 (1973) 285-292, which are incorporated herein by reference in their entireties.

In one or more embodiments, the oxygen carrier material may exhibit properties known in the industry as "Geldart A" properties. In other embodiments, the oxygen carrier material may exhibit properties known in the industry as "Geldart B" properties.

Group A is understood by those skilled in the art as representing an aeratable powder, having a bubble-free range of fluidization; a high bed expansion; a slow and linear deaeration rate; bubble properties that may include a predominance of splitting/recoalescing bubbles, with a maximum bubble size and large wake; high levels of solids mixing and gas backmixing, assuming equal U-Umf (U is the velocity of the carrier gas, and Umf is the minimum fluidization velocity, typically though not necessarily measured in meters per second, m/s, i.e., there is excess gas velocity); axisymmetric slug properties; and no spouting, except in very shallow beds. The properties listed tend to improve as the mean particle size decreases, assuming equal dp; or as the <45 micrometers (μm) proportion is increased; or as pressure, temperature, viscosity, and density of the gas increase. In general, the particles may exhibit a small mean particle size and/or low particle density (<1.4 grams per cubic centimeter, g/cm3), fluidize easily, with smooth fluidization at low gas velocities, and may exhibit controlled bubbling with small bubbles at higher gas velocities.

Group B is understood by those skilled in the art as representing a "sand-like" powder that starts bubbling at Umf; that exhibits moderate bed expansion; a fast deaeration; no limits on bubble size; moderate levels of solids mixing and gas backmixing, assuming equal U-Umf; both axisymmetric and asymmetric slugs; and spouting in only shallow beds. These properties tend to improve as mean particle size decreases, but particle size distribution and, with some uncertainty, pressure, temperature, viscosity, or density of gas seem to do little to improve them. In general, most of the particles having a particle size (dp) of 40 μm<dp<500 μm when the density (ρp) is 1.4<ρp<4 g/cm3, and preferably 60 μm<dp<500 μm when the density (ρp) is 4 g/cm3 and 250 μm<dp<100 μm when the density (ρp) is 1 g/cm3.

In one or more embodiments, the dehydrogenation catalyst may include gallium, chromium, and/or platinum. As described herein, a gallium and/or platinum dehydrogenation catalyst comprises gallium, platinum, or both. The dehydrogenation catalyst may be carried by an alumina or alumina silica support, and may optionally comprise potassium. In one or more embodiments, the dehydrogenation catalysts may include catalysts disclosed in U.S. Pat. No. 8,669,406, which is incorporated herein by reference in its entirety, such as those including Ga, Cr, and/or Fe based catalysts. According to additional embodiments, Pt based catalysts may be utilized. In one or more embodiments, those catalysts disclosed in EP 0948475B1 and/or WO 2010/133565, which are each incorporated herein by reference in its entirety, may be utilized. Additional catalyst embodiments contemplated as suitable for use in the systems and methods described herein include those of U.S. Pat. No. 8,669,406, which is incorporated herein by reference in its entirety. Such catalysts may contain relatively low amounts of Cr, such as less than 6%, or approximately 1.5%. However, it should be understood that other suitable dehydrogenation catalysts may be utilized to perform the dehydrogenation reaction.

In one or more embodiments, the dehydrogenation catalyst may exhibit suitable stability when in the presence of steam. As is described herein, the combustion of hydrogen may form steam, which may be in direct contact with the dehydrogenation catalyst. It is contemplated that not all dehydrogenation catalysts are equally effective in steam environments. In one or more embodiments, dehydrogenation catalysts are utilized which maintain a substantial amount of their reactivity and/or selectivity for the dehydrogenation of light alkanes. For example, one or more of the dehydrogenation catalysts utilized in the presently disclosed systems and methods may not deteriorate in alkane conversion and/or selectivity for dehydrogenation more than 25%, more than 20%, more than 15%, more than 10%, more than 5%, or may even have improved alkane conversion and/or selectivity for dehydrogenation when in the presence of steam in amounts consistent with the operation of the presently disclosed systems. In some embodiments, the dehydrogenation catalyst may function with such conversion and/or selectivity when exposed to at least 10 mol % water (such as from 10 mol. % to 50 mol. % water) for a period of up to, e.g., 120 seconds (the time which the catalyst may be exposed to such conditions, according to some embodiments of the presently disclosed system).

Suitable examples of dehydrogenation catalysts may be prepared such that it meets the Geldart A definition. In some embodiments, the dehydrogenation catalyst comprises gallium and platinum supported on alumina in the delta or theta phase, or in a mixture of delta plus theta phases, or theta plus alpha phases, or delta plus theta plus alpha phases, modified with silica, and having a surface area preferably less than about 100 square meters per gram (m2/g), as determined by the BET method. In other embodiments, the dehydrogenation catalyst comprises: from 0.1 to 34 wt. %, preferably 0.2 to 3.8 wt. %, gallium oxide ($Ga_2O_3$); from 1 to 300 parts per million (ppm), preferably 50 to 300 ppm, by weight platinum; from 0 to 5 wt. %, preferably 0.01 to 1 wt. %, of an alkaline and/or earth-alkaline such as potassium; from 0.08 to 3 wt. % silica; the balance to 100 wt. % being alumina.

As stated previously, within the fluidized bed reactor 110, the hydrogen may be contacted with an oxygen-rich oxygen carrier material. The oxygen carrier material may include one or more transition metal oxides. According to one or more embodiments, the one or more transition metal oxides may be a redox-active transition metal oxide. The redox-active transition metal oxide includes binary, ternary, or other mixed metal oxides capable of undergoing reduction in the presence of a reducing agent (for example, hydrogen) and oxidation in the presence of oxidizing agent (for example, oxygen or air). In some embodiments the redox-active transition metal oxide may be chosen from $Mn_2O_3$, $Fe_2O_3$, $Co_3O_4$, $CuO$, $(LaSr)CoO_3$, $(LaSr)MnO_3$, $Mg_6MnO_8$, $MgMnO_3$, $MnO_2$, $Fe_3O_4$, $Mn_3O_4$, and $Cu_2O$. In some embodiments, the oxygen carrier material may be a solid. In specific embodiments, the oxygen carrier material may be a crushed solid or powder.

In one or more embodiments, the oxygen carrier material may include a hydrogen-selective oxygen carrier material that may have a core material and a shell material. In some embodiments, the core material may include a redox-active transition metal oxide. The redox-active transition metal oxide may include binary, ternary, or other mixed metal oxides capable of undergoing reduction in the presence of a reducing agent (for example, hydrogen) and oxidation in the presence of oxidizing agent (for example, oxygen or air). In some embodiments the redox-active transition metal oxide may be chosen from $Mn_2O_3$, $Fe_2O_3$, $Co_3O_4$, CuO, (LaSr)$CoO_3$, (LaSr)$MnO_3$, $Mg_6MnO_8$, $MgMnO_3$, $MnO_2$, $Fe_3O_4$, $Mn_3O_4$, and $Cu_2O$. As stated previously, the hydrogen-selective oxygen carrier material may have a shell material. The shell material may impart selectivity towards hydrogen combustion. The shell material may include one or more alkali transition metal oxides. The one or more alkali transition metal oxides may include one or more alkali elements and transition metals. In some embodiments, alkali elements may include one or more of sodium (Na), lithium (Li), potassium (K), and cesium (Cs). In some embodiments, transition metals may include one or more of tungsten (W) and molybdenum (Mo). In further embodiments, the one or more alkali transition metal oxides are chosen from $Na_2WO_4$, $K_2MoO_4$, $Na_2MoO_4$, $KZWO_4$, $Li_2WO_4$, $CsWO_4$, and $Li_2MoO_4$. For example, oxygen carrier materials such as those disclosed in U.S. App. No. 62/725,504, entitled "METHODS OF PRODUCING HYDROGEN-SELECTIVE OXYGEN CARRIER MATERIALS," filed on, Aug. 31, 2018, and U.S. App. No. 62/725,508, entitled "HYDROGEN-SELECTIVE OXYGEN CARRIER MATERIALS AND METHODS OF USE," filed on, Aug. 31, 2018, are contemplated as suitable for the presently disclosed processes, and the teachings of these references are incorporated by reference herein.

In one or more additional embodiments, the oxygen carrier material may include those of U.S. Pat. Nos. 5,430,209, 7,122,495, and/or WO 2018/232133, each of which are incorporated by reference in their entireties.

The oxygen-rich oxygen carrier material may be reducible by releasing oxygen that may be selective for combusting hydrogen. For example, the oxygen carrier material may be selective for the combustion of hydrogen over hydrocarbons. In some embodiments, the oxygen-rich oxygen carrier material comprises from about 1 wt. % to about 20 wt. % releasable oxygen based on total weight of the oxygen-rich oxygen carrier material. In other embodiments, the oxygen-rich oxygen carrier material comprises from about 1 wt. % to about 10 wt. %, from about 1 wt. % to about 5 wt. %, from about 5 wt. % to about 20 wt. %, or from about 5 wt. % to about 10 wt. % releasable oxygen. As described herein, "releasable oxygen" may refer to the oxygen that can be released through redox by the oxygen-carrier material. Other oxygen may be present in the oxygen-carrier material that is not releasable through redox. It should be understood that in some embodiments, the oxygen may be released from a surface of the oxygen carrier material simultaneously with the combustion of hydrogen at the surface of the oxygen carrier material.

As stated previously, the releasable oxygen of the oxygen-rich oxygen carrier materials may be selective for combusting hydrogen over hydrocarbons. In some embodiments, at least about 60% of the releasable oxygen of the oxygen carrier material is selective for hydrogen combustion. In other embodiments, at least about 55% of the releasable oxygen of the oxygen carrier material is selective for hydrogen combustion.

In embodiments, when the hydrogen is contacted by the oxygen-rich oxygen carrier material, some of the releasable oxygen is removed from the oxygen-rich oxygen carrier material. In some embodiments, contacting the hydrogen with the oxygen-rich oxygen carrier material removes from about 1 wt. % to 50 wt. % of the releasable oxygen from the oxygen-rich oxygen carrier material. In other embodiments, contacting the hydrogen with the oxygen-rich oxygen carrier material removes from about 10 wt. % to about 50 wt. %, from about 10 wt. % to about 25 wt. %, or from about 25 wt. % to about 50 wt. % of the releasable oxygen from the oxygen-rich oxygen carrier material.

In further embodiments, when the hydrogen is contacted by the oxygen-rich oxygen carrier material, the oxygen-rich oxygen carrier material combusts greater than about 50% of the hydrogen. In other embodiments, when the hydrogen is contacted by the oxygen-rich oxygen carrier material, the oxygen-rich oxygen carrier material combusts about 50% to about 90%, or about 75% to about 90% of the hydrogen that is produced.

The contacting of the oxygen-rich oxygen carrier material with the hydrogen may combust the hydrogen and form an oxygen-diminished oxygen carrier material. To form the oxygen-diminished oxygen carrier material, at least a portion of the oxygen-rich oxygen carrier material may be reduced to a lower oxidation state. Once the oxygen carrier material has been reduced to form the oxygen-diminished oxygen carrier material, the oxygen-diminished oxygen carrier material may be discharged from the fluidized bed reactor 110 at a lower oxidation state.

Still referring to FIG. 1, one or more of the dehydrogenation catalyst, the oxygen-diminished oxygen carrier material, the oxygen-diminished dual-purpose material, and the gas products may be separated within the fluidized bed reactor 110 by high efficiency cyclones. In embodiments described, the oxygen-diminished oxygen carrier material may be passed to the regeneration unit 120 via stream 103. The dehydrogenation catalyst may also be passed to the regeneration unit 120 via the stream 103. However, it is contemplated that the dehydrogenation catalyst and the oxygen-diminished oxygen carrier material may be passed via separate streams. In further embodiments, the dehydrogenation catalyst, the oxygen carrier material, or both may be stripped with a displacement gas such as nitrogen, steam, methane, natural gas or other suitable gas before being sent to a regeneration unit 120. In some embodiments, the dehydrogenation catalyst may be slightly deactivated after contacting the hydrocarbon feed 101. In other embodiments, the dehydrogenation catalyst may still be suitable for reaction in the fluidized bed reactor 110. As used herein, "deactivated" may refer to a catalyst that is contaminated with a substance such as coke, or is cooler in temperature than needed to promote reaction of the feed.

Regeneration may remove the contaminant such as coke, raise the temperature of the catalyst, or both. In some embodiments, use of a reconstituted catalyst may offer renewed or regenerated activity where the dehydrogenation catalyst may exhibit reduced activity due to use, particularly where it has been used in a dehydrogenation such as is described herein, such that yield (activity) has been measurably reduced. In the case of a propane dehydrogenation, for example, the used or spent ("at least partially deactivated") dehydrogenation catalyst may be reconstituted and cycled back into the reactor system 100, where the dehydrogenation catalyst may exhibit a propane dehydrogenation activity that is at least 2% absolute propane conversion greater than that of the at least partially deactivated dehydrogenation catalyst under otherwise identical dehydrogenation conditions. In another embodiment the propane dehydrogenation activity exhibited by the reconstituted dehydrogenation catalyst may be greater by an amount equal to or more than 5% on the same basis.

In some embodiments, coke on the at least partially deactivated dehydrogenation catalyst may be removed by combustion in an oxygen-containing environment in the regeneration unit 120. In some embodiments, the oxygen-containing environment may be air. In further embodiments, the dehydrogenation catalyst may be heated by additional fuel to a target temperature. The dehydrogenation catalyst may then circulate back to the fluidized bed reactor 110, carrying the necessary heat for the dehydrogenation reaction. For additional generalized information on catalytic dehydrogenations carried out in circulating fluidized beds, those skilled in the art are referred to, for example, US Patent Publication 2005/0177016 A1; International Patent Publication WO 2005/077867 (corresponding to US Patent Publication 2008/0194891 A1); and International Patent Publication WO 20107591 A1.

In some embodiments, the oxygen-diminished oxygen carrier material may be re-oxidized to an oxidation state higher than the oxidation state of the oxygen-diminished oxygen carrier material by combustion in an oxygen-containing environment in the regeneration unit 120. In some embodiments, the oxygen-containing environment may be air. In some embodiments of forming the oxygen-rich oxygen carrier material, the oxygen-diminished oxygen carrier material may be restored to its original oxidation state. In some embodiments, the oxygen-diminished oxygen carrier material may have an oxidation state of +2, +3, or +4. The oxygen-rich oxygen carrier material may then circulate back to the fluidized bed reactor 110, carrying the necessary heat for the dehydrogenation reaction. In other embodiments, nitrogen or steam may also be used to convey the oxygen-rich oxygen carrier material to the fluidized bed reactor 110. The resulting gas stream from the regeneration unit 120 consists of air depleted of or containing a lower concentration of $O_2$.

In one or more embodiments, a supplemental fuel may be combusted in the regeneration unit 120 to produce heat and increase the temperature of one or more of the oxygen-rich oxygen carrier material or the dehydrogenation catalyst. The heat produced by the oxidizing of the oxygen-diminished oxygen carrier material and the combusting of the supplemental fuel may be sufficient to maintain the temperature of the fluidized bed reactor at a desired temperature. The desired temperature may depend upon the minimum temperature needed for operation of the fluidized bed reactor 110, since the oxygen carrier material and the dehydrogenation catalyst may enter the fluidized bed reactor 110 and impart their temperature to the fluidized bed reactor 110.

In one or more embodiments, the regeneration unit 120 may operate at a temperature of 650° C., or even 700° C., to 900° C., such as 725° C. to 875° C., or 750° C. to 850° C. Generally, the regeneration unit 120 may have a temperature of at least 50° C. greater than that of the fluidized bed reactor 110. Such a temperature range may be utilized so that the temperature of the fluidized bed reactor 110 may be maintained with a limited amount of dehydrogenation catalyst and/or oxygen carrier material. Additionally, such temperatures may be needed to activate the dehydrogenation catalyst.

Still referring to FIG. 1, the oxygen-rich oxygen carrier material and the dehydrogenation catalyst may be passed from the regeneration unit 120 to the fluidized bed reactor 110 via stream 104. However it is contemplated that the dehydrogenation catalyst and the oxygen-rich oxygen carrier material may be passed via separate streams. As such, one or more of the dehydrogenation catalyst and the oxygen carrier may be looped or recycled through the reactor system 100.

Figure 2:
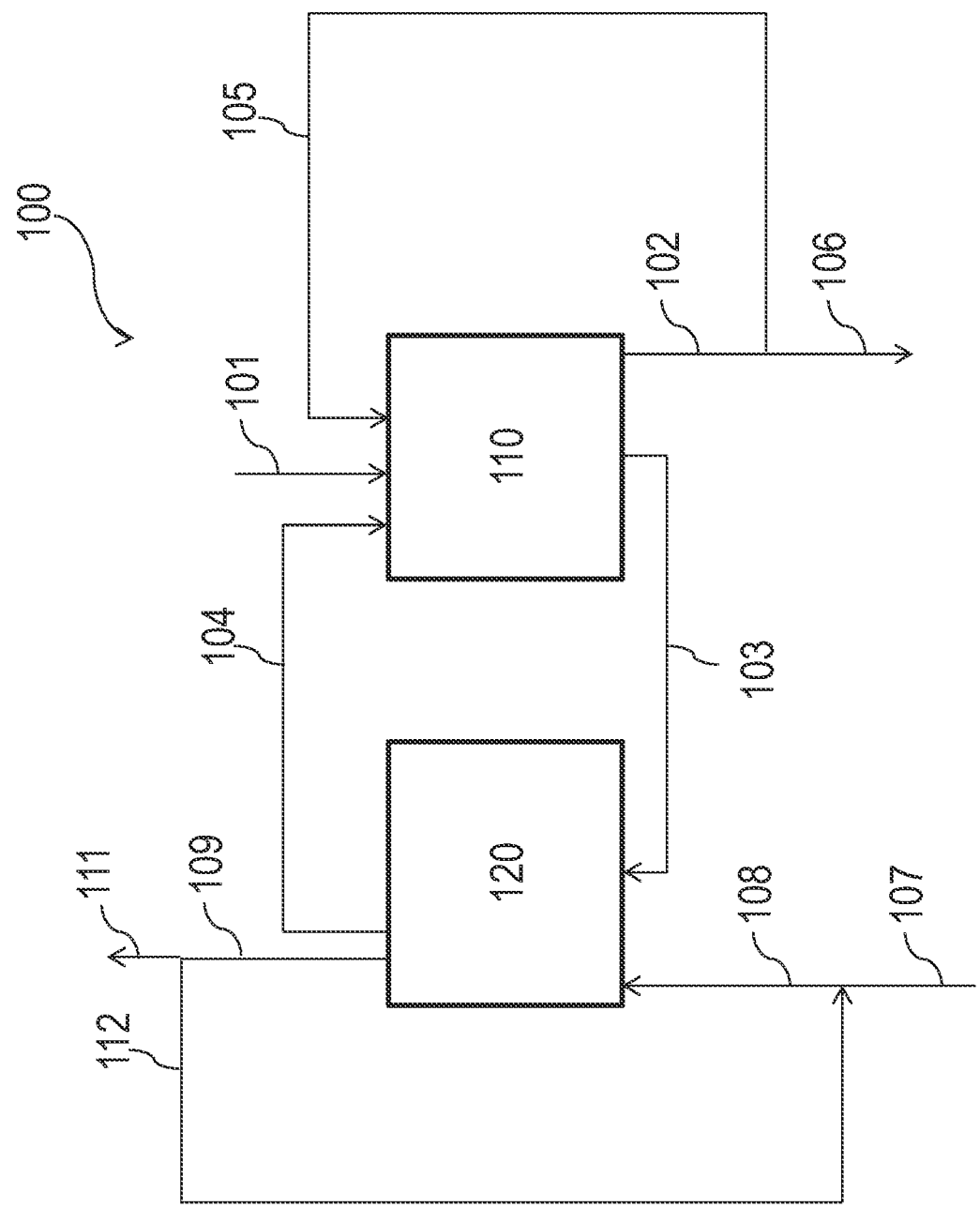
FIG. 2 schematically depicts a catalytic dehydrogenation system with recycle, according to one or more embodiments described herein.

Now referring to FIG. 2, in one or more embodiments presently described, the re-oxidation of the oxygen-diminished oxygen carrier material may be controlled. For example, according to one embodiment, a flue gas may be passed into the regeneration unit 120 via stream 108. In some embodiments, the flue gas may be a recycle stream from a neighboring chemical process. In some embodiments, the oxygen-diminished oxygen carrier material may be re-oxidized to an oxidation state higher than the oxidation state of the oxygen-diminished oxygen carrier material by at least a portion of the flue gas exiting the regeneration unit 120 via stream 109 that is recycled to the regeneration unit 120 via stream 112. The stream 109 exiting the regeneration unit 120 may include air depleted of oxygen or containing a lower concentration of oxygen. In some embodiments, stream 112 may be mixed with fresh air via stream 107 to form stream 108. In some embodiments, stream 108 may include at least 25 mole percent (mol %) oxygen. In other embodiments, stream 108 may include from about 4 mol % to about 25 mol % oxygen, from about 4 mol % to about 21 mol %, from 4 mol % to about 10 mol % oxygen, from 10 mol % to about 25 mol % oxygen, or from 10 mol % to about 21 mol % oxygen.

In embodiments, by contacting the flue gas with the oxygen-rich oxygen carrier material, some of the releasable oxygen is removed from the oxygen-rich oxygen carrier material. In some embodiments, contacting the flue gas with the oxygen-rich oxygen carrier material removes from about 0 wt. % to 15 wt. % of the releasable oxygen from the oxygen-rich oxygen carrier material. In other embodiments, contacting the hydrogen with the oxygen-rich oxygen carrier material removes from about 0 wt. % to about 10 wt. %, from about 0 wt. % to about 5 wt. %, or from about 5 wt. % to about 10 wt. % of the releasable oxygen from the oxygen-rich oxygen carrier material.

In other embodiments, the oxygen-diminished oxygen carrier material may be partially re-oxidized to an oxidation state higher than the oxidation state of the oxygen-diminished oxygen carrier material in the regeneration unit 120. In some embodiments, the oxygen-rich oxygen carrier material comprises less releasable oxygen than the maximum releasable oxygen capacity of the oxygen carrier material.

In another embodiment, the oxygen-rich oxygen carrier material may also be reduced to a lower oxidation state ("at least partially reduced") by combusting the oxygen-rich oxygen carrier material with a reducing gas. Without being bound by theory, in some embodiments, at least partially reducing the oxygen-rich oxygen carrier material may precondition the oxygen carrier material to maximize the selectivity of the fluidized bed reactor 110. The releasable oxygen bound on the surface of the oxygen carrier material may be less selective for hydrogen combustion than the remaining bulk oxygen. In further embodiments, the oxygen-rich oxygen carrier material may be at least partially reduced after passing from regeneration unit 120 and before passing to the fluidized bed reactor 110 in a reducer. In some embodiments, a fuel source may be used to at least partially reduce the oxygen-rich oxygen carrier material, where a fuel source pre-combusts the oxygen that was chemically-absorbed during re-oxidation of the oxygen-diminished oxygen carrier material in the regeneration unit 120. Depending on the configuration of the reducer, products formed by the pre-combustion may exit the reactor system 100 via a stream 102, or alternatively products formed by the pre-combustion may exit the regenerator unit 120 (such as, for example, via line 111 in FIG. 2), or at any location along line 104. In some embodiments, the products formed by the pre-combustion may be stripped from one of the process stream by, for example, nitrogen, steam or air. In some embodiments, the pre-combustion may reduce the amount of reducible oxygen on the oxygen carrier and free oxygen between 0.01 to 10%. Without being bound by any particular theory, this oxygen is expected to be the most unselective to hydrogen combustion.

In some embodiments, product gas from the fluidized bed reactor 110 may be passed out of the fluidized bed reactor 110 via stream 102. Stream 102 may be further processed such as by one or more subsequent separation steps or further reacted. It is contemplated that stream 102 may be utilized as a feed for another reactor system or sold as a chemical product.

Still referring to FIG. 1, the reactor system 100 may be used to dehydrogenate hydrocarbons to produce olefins and other products (e.g., styrene from ethylbenzene), which may exit the fluidized bed reactor 110 via stream 102. In one or more embodiments, stream 102 may comprise one or more olefins and other products. Stream 102 may comprise one or more of ethylene, propylene, butylene, or styrene. According to one or more embodiments, stream 102 may comprise at least 50 wt. %, at least 60 wt. %, at least 70 wt. %, at least 80 wt. %, at least 90 wt. %, at least 95 wt. % or even at least 99 wt. % of ethylene. In additional embodiments, stream 102 may comprise at least 50 wt. %, at least 60 wt. %, at least 70 wt. %, at least 80 wt. %, at least 90 wt. %, at least 95 wt. % or even at least 99 wt. % of propylene. In additional embodiments, stream 102 may comprise at least 50 wt. %, at least 60 wt. %, at least 70 wt. %, at least 80 wt. %, at least 90 wt. %, at least 95 wt. % or even at least 99 wt. % of the sum of ethylene and propylene.

In one or more embodiments, heat gained or lost through the dehydrogenation reaction, the re-oxidation of the oxygen-diminished oxygen carrier material, and the reduction of the oxygen-rich oxygen carrier material may create or use heat (i.e., be exothermic or endothermic). In one or more embodiments, the contacting of the hydrocarbon feed with the dehydrogenation catalyst may be endothermic and results in a dehydrogenation heat loss. In some embodiments, the contacting of the hydrogen with the oxygen-rich oxygen carrier material may be exothermic and results in a combustion heat gain. The re-oxidizing of the oxygen-diminished oxygen carrier material may be exothermic and results in an oxygenation heat gain. As such, by incorporating hydrogen combustion during catalytic dehydrogenation, in some embodiments, enough heat may be generated during the re-oxidation of the oxygen-diminished oxygen carrier material to act as a source of heat for the alkane to olefin reaction. As such, embodiments of the disclosed process may allow for higher alkane conversion while reducing or eliminating needs for fuel gas, as required for conventional cracking because the heat gained throughout the process by the re-oxidizing of the oxygen carrier material, the combustion of hydrogen, or both may produce the amount of heat required for the alkanes or alkyl aromatics to olefins reaction.

As presently described, the "dehydrogenation heat loss" refers to the amount of heat lost by the dehydrogenation of the feed alkanes, the "combustion heat gain" refers to the amount of heat created by the combustion of the hydrogen, and the "oxygenation heat gain" refers to the amount of heat created by the oxidation of the oxygen-diminished oxygen carrier material. In one or more embodiments, the combustion heat gain may contribute heat to the system that account for at least a portion of the dehydrogenation heat loss. In additional embodiments, supplemental fuel may be combusted to heat one or more of the dehydrogenation catalyst or the oxygen carrier material. The supplemental fuel may make up for any shortcoming in heat created by the combustion of the hydrogen or the oxygenation of the oxygen carrier material. However, it should be understood that in the embodiments disclosed, the amount of necessary supplemental fuel may be substantially less than would be necessary in a system that did not incorporate an oxygen carrier material.

Still referring to FIG. 1, in additional embodiments, a dual purpose material may be utilized in replacement or along with separate oxygen carrier materials and dehydrogenation catalysts. It should be understood that, according to one or more embodiments, the dual purpose material may function as a dehydrogenation catalyst and as an oxygen carrier material, and may operate at identical or similar processing conditions such as, but not limited to, temperature, pressure, residence time, superficial velocity, space velocity, solids flux, etc. Other process flows, such as the reactant gas and product gas, may flow through the system of FIG. 1 as previously described when the oxygen carrier material and dehydrogenation catalyst are utilized. It should also be appreciated that the dual-purpose material may be utilized in the embodiments described with respect to FIG. 1 in terms of re-oxygenation and de-oxygenation, and the thermodynamic consequences of such. For example, the use of flue gas in the regeneration is contemplated in the embodiments utilizing the presently disclosed dual-purpose material.

In one or more embodiments, the dual purpose material may comprise dehydrogenation catalyst and oxygen carrier material, as described herein. For example, the dual purpose material may be a composite of spray dried or otherwise co-formed dehydrogenation catalyst and oxygen carrier material.

In additional embodiments, the reactive mechanisms of the dual purpose material may be different from that of separate dehydrogenation catalysts and oxygen carrier materials described herein. For example, it is contemplated that in some embodiments an oxygen molecule, such as an oxygen radical, which is releasable oxygen from the dual purpose material, may catalyze the dehydrogenation reaction and instantaneously react with the released hydrogen from the reactant hydrocarbon to form water. According to one or more embodiments, a dual purpose material may be fed into the fluidized bed reactor 110. The chemical feed may contact the dual purpose material in the fluidized bed reactor 110. Each of the chemical feed and the dual purpose material may flow upwardly into and through the fluidized bed reactor 110 to produce a chemical product and an oxygen-diminished dual purpose material. The dual-purpose material may contact the hydrocarbon feed in the fluidized bed reactor 110 and produce a dehydrogenated product. The oxygen-rich dual-purpose material may be reducible by releasing oxygen. The hydrogen released from the chemical feed during dehydrogenation may be reacted with released oxygen from the oxygen-rich dual-purpose material. For example, in one embodiment hydrogen gas is released and is later contacted with the dual-purpose material which combusts the hydrogen with releasable oxygen from the oxygen-rich dual-purpose material to form steam. The contacting of the dual-purpose material with the hydrocarbon feed may produce a dehydrogenated product and hydrogen. Additionally, within the fluidized bed reactor 110, the hydrogen may be contacted with the oxygen-rich dual purpose material in the fluidized bed reactor. The oxygen-rich dual purpose material may comprise releasable oxygen and be reducible. The contacting of the oxygen-rich dual purpose material with the hydrogen may combust the hydrogen and form an oxygen-diminished dual purpose material. In another embodiment, the released hydrogen is never present as a gas and is instead instantly formed into water by combination with the releasable oxygen.

Similar to as described in the context of the use of a dehydrogenation catalyst and oxygen carrier material, the dual purpose material and the chemical product may be passed to a separation device in a separation section within the fluidized bed reactor 110. The oxygen-diminished dual purpose material may be separated from the chemical product in the separation device within the fluidized bed reactor 110.

In some embodiments, the hydrocarbon feed may contact the oxygen-rich dual purpose material in an upstream reactor section of the fluidized bed reactor 110. The chemical feed and the oxygen-rich dual purpose material may flow upwardly into and through the downstream reactor section of the fluidized bed reactor 110 to produce a chemical product and an oxygen-diminished dual purpose material.

In one or more embodiments, the dual purpose material may include solid particulate catalyst types that are capable of fluidization. In some embodiments, the dual purpose material may exhibit properties known in the industry as "Geldart A" properties. The dual purpose material may include one or more materials that are included in the disclosed dehydrogenation catalysts, oxygen carrier materials, or both. In some embodiments, the dual purpose material may be hydrogen-selective for combustion (i.e., selective over hydrocarbons).

In embodiments, when the hydrogen is contacted by the oxygen-rich dual purpose material, some of the releasable oxygen is removed from the oxygen-rich dual purpose material. In some embodiments, contacting the hydrogen with the oxygen-rich dual-purpose material removes from about 1 wt. % to 50 wt. % of the releasable oxygen from the oxygen-rich dual-purpose material. In other embodiments, contacting the hydrogen with the oxygen-rich dual purpose material removes from about 10 wt. % to about 50 wt. %, from about 10 wt. % to about 25 wt. %, or from about 25 wt. % to about 50 wt. % of the releasable oxygen from the oxygen-rich dual purpose material. In further embodiments, when the hydrogen is contacted by the oxygen-rich dual purpose material, the oxygen-rich dual purpose material converts greater than about 50% of the hydrogen produced by dehydrogenation (either instantaneously by reaction of atomic hydrogen with released oxygen or by later combustion reaction of hydrogen gas). In other embodiments, when the hydrogen is contacted by the oxygen-rich dual purpose material, the oxygen-rich dual purpose material combusts about 50% to about 90%, or about 75% to about 90% of the hydrogen.

The contacting of the oxygen-rich dual purpose material with the hydrogen may combust the hydrogen and form an oxygen-diminished dual purpose material. To form the oxygen-diminished dual purpose material, at least a portion of the oxygen-rich dual purpose material may be reduced to a lower oxidation state. Once the dual purpose material has been reduced to form the oxygen-diminished dual purpose material, the oxygen-diminished dual purpose material may be discharged from the fluidized bed reactor 110 at a lower oxidation state.

Still referring to FIG. 1, Similar to as described in the context of the use of a dehydrogenation catalyst and oxygen carrier material, the oxygen-diminished dual purpose material and the gas products may be separated within the fluidized bed reactor 110 by high efficiency cyclones. In embodiments described, the oxygen-diminished dual purpose material may be passed to the regeneration unit 120 via stream 103.

In some embodiments, the dual purpose material may be slightly deactivated after contacting the hydrocarbon feed 101. In other embodiments, the dual purpose material may still be suitable for reaction in the fluidized bed reactor 110. The dual purpose material may be similarly regenerated as described herein with respect to the dehydrogenation catalyst, such as by the removal of coke and/or change in temperature.

In some embodiments, the oxygen-diminished dual purpose material may be re-oxidized to an oxidation state higher than the oxidation state of the oxygen-diminished dual purpose material by oxidation in an oxygen-containing environment in the regeneration unit 120. In some embodiments, the oxygen-containing environment may be air. In some embodiments of forming the oxygen-rich dual purpose material, the oxygen-diminished dual purpose material may be restored to its original oxidation state. In some embodiments, the oxygen-diminished dual purpose material may have an oxidation state of, for example, +2, +3, or +4, or even greater. The oxygen-rich dual purpose material may then circulate back to the fluidized bed reactor 110, carrying the necessary heat for the dehydrogenation reaction. In other embodiments, nitrogen or steam may also be used to convey the oxygen-rich dual purpose material to the fluidized bed reactor 110. The resulting gas stream from the regeneration unit 120 consists of air depleted of or containing a lower concentration of $O_2$.

Still referring to FIG. 1, the oxygen-rich dual purpose material may be passed from the regeneration unit 120 to the fluidized bed reactor 110 via stream 104. As such, the dual purpose material may be looped or recycled through the reactor system 100. In some embodiments, the dual purpose material may be partially reduced in a pre-treatment reduction step as described herein with respect to the oxygen carrier material.

Now referring to embodiments of the process depicted in FIG. 2, stream 102 or a portion of stream 102 may be passed back to the fluidized bed reactor 110 via product recycle stream 105. In some embodiments, stream 102 may include one or more unreacted alkanes or alkyl aromatics. In further embodiments, the one or more unreacted alkanes or alkyl aromatics may be passed out of the fluidized bed reactor 110 to a separation unit (not pictured) via stream 102. The one or more unreacted alkanes or alkyl aromatics may be separated from a remainder of the dehydrogenation effluent using the separation unit. In some embodiments, the one or more unreacted alkanes or alkyl aromatics may then be transported out of the separation unit and passed to the fluidized bed reactor 110 via product recycle stream 105. In some embodiments from about 10% to about 90% of the one or more unreacted alkanes or alkyl aromatics may be passed via product recycle stream 105 to the fluidized bed reactor 110. In other embodiments, from about 20% to about 90%, from about 30% to about 90%, from about 40% to about 90%, from about 50% to about 90%, from about 60% to about 90% from about 70% to about 90%, or from about 80% to about 90% of the one or more unreacted alkanes or alkyl aromatics may be passed via product recycle stream 105 to the fluidized bed reactor 110.

Figure 3:
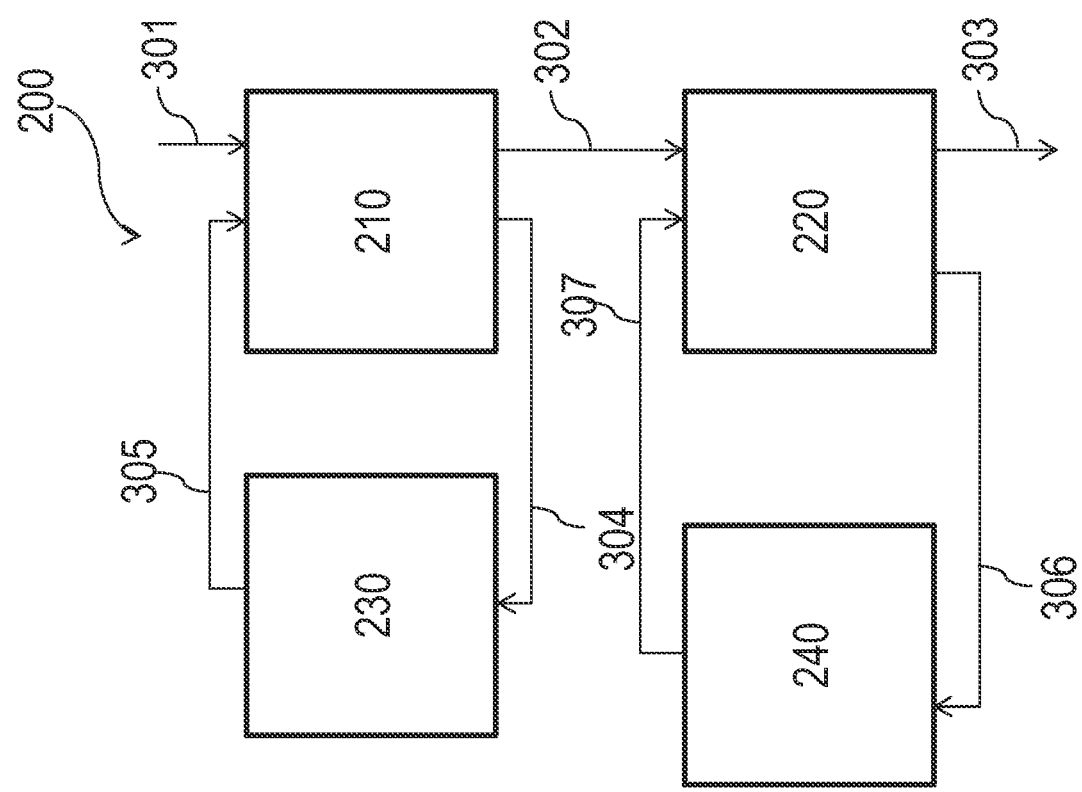
FIG. 3 schematically depicts a catalytic dehydrogenation system with separate dehydrogenation and hydrogen combustion reactors, according to one or more embodiments described herein.

As depicted in FIG. 3, a hydrocarbon feed stream 301 may enter the reactor system 200 and be processed to form a stream 303. In the reactor system 200, the components of the hydrocarbon feed stream 301 may contact the dehydrogenation catalyst and oxygen carrier material in separate reactors (i.e., first fluidized bed reactor 210 and second fluidized bed reactor 220 arranged in series). It should be understood that the hydrocarbon feed stream 301 may include chemical compositions that are the same as those described herein with respect to the hydrocarbon feed 101.

As depicted in FIG. 3, the hydrocarbon feed may be passed to a first fluidized bed reactor 210. The first fluidized bed reactor 210 may operate with same conditions (e.g., temperature and pressure) as was disclosed with respect to the fluidized bed reactor 110 of FIG. 1, and where the solids in first fluidized bed reactor 210 may include or consist essentially of the dehydrogenation catalyst. In other embodiments, the first fluidized bed reactor 210 may operate with conditions (e.g. temperature and pressure) that control the dehydrogenation of the hydrocarbon feed 301. In embodiments, the hydrocarbon feed 301 may be contacted with a dehydrogenation catalyst in the first fluidized bed reactor 210. The contacting of the dehydrogenation catalyst with the hydrocarbon feed 310 may produce a dehydrogenation effluent. The dehydrogenation effluent may comprise hydrogen.

As depicted in FIG. 3, the dehydrogenation catalyst in the first fluidized bed reactor 210 may be passed to a regeneration unit 230 via stream 304, be regenerated in regeneration unit 230, and subsequently passed back to the first fluidized bed reactor 210. As was described previously with respect to the regeneration unit 120, the dehydrogenation catalyst may be heated in the regeneration unit 230, coke or other contaminants may be removed from the dehydrogenation catalyst, or both. In some embodiments, supplemental fuel may be added to the regeneration unit 230 to provide heat.

The dehydrogenation effluent may be passed via stream 302 to a second fluidized bed reactor 220. The second fluidized bed reactor 220 may operate with same conditions (e.g., temperature and pressure) as was disclosed with respect to the fluidized bed reactor 110 of FIG. 1, and where the solids in second fluidized bed reactor 220 may include, or consist essentially of, the oxygen carrier material. Within the second fluidized bed reactor 220, the hydrogen of the dehydrogenation effluent may be contacted with an oxygen-rich oxygen carrier material. The contacting of the hydrogen and the oxygen-rich oxygen carrier material may combust at least a portion of the hydrogen, produce a combustion effluent, and form an oxygen-diminished oxygen carrier material.

The oxygen-diminished oxygen carrier material in the second fluidized bed reactor 220 may be passed to a second regeneration unit 240 via stream 306, be oxygenated in the second regeneration unit 240, and subsequently passed back to the second fluidized bed reactor 220. As was described previously with respect to the regeneration unit 120, the oxidizing of the oxygen-diminished oxygen carrier material in the second regeneration unit 240 may form the oxygen-rich oxygen carrier material.

In additional embodiments, the combustion effluent via stream 303 or a portion of stream 303 may be passed back to the first fluidized bed reactor 210 via product recycle stream (not depicted in FIG. 3). In some embodiments, the combustion effluent may include one or more unreacted alkanes or alkyl aromatics. In further embodiments, combustion effluent comprising the one or more unreacted alkanes or alkyl aromatics, may be passed out of the second fluidized bed reactor 220 to a separation unit (not pictured) via stream 303. The one or more unreacted alkanes or alkyl aromatics may be separated from a remainder of the combustion effluent using the separation unit. In some embodiments, the one or more unreacted alkanes or alkyl aromatics may then be transported out of the separation unit and passed to the first fluidized bed reactor 210. In some embodiments from about 10% to about 90% of the one or more unreacted alkanes or alkyl aromatics may be passed to the first fluidized bed reactor 210. In other embodiments, from about 20% to about 90%, from about 30% to about 90%, from about 40% to about 90%, from about 50% to about 90%, from about 60% to about 90% from about 70% to about 90%, or from about 80% to about 90% of the one or more unreacted alkanes or alkyl aromatics may be passed via product recycle stream to the first fluidized bed reactor 210 (similar to stream 105 in the embodiment of FIG. 2).

Figure 4:
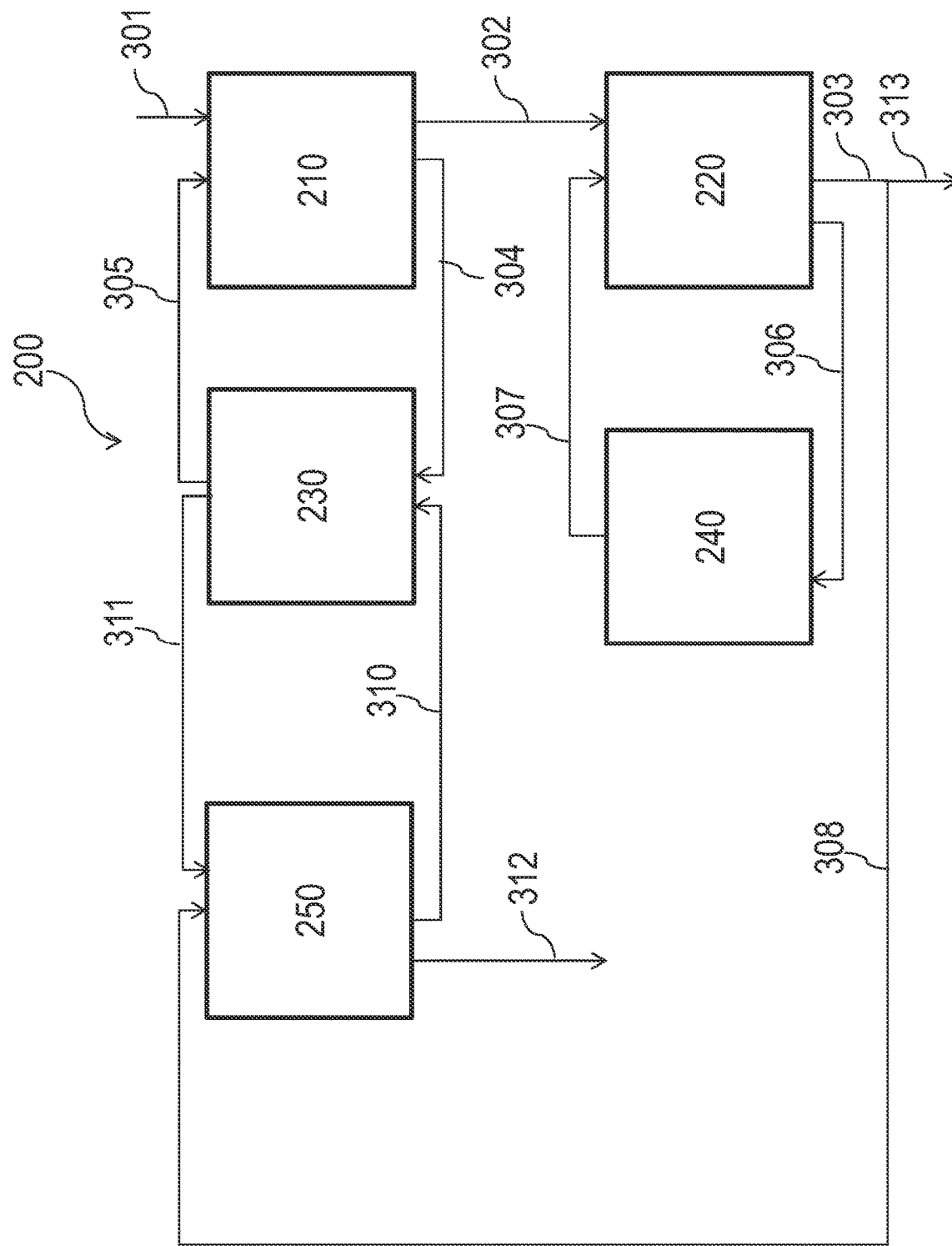
FIG. 4 schematically depicts a catalytic dehydrogenation system with separate dehydrogenation and hydrogen combustion reactors and a second dehydrogenation reactor, according to one or more embodiments described herein.

Now referring to FIG. 4, according to one or more embodiments, a process similar to that described in FIG. 3 may further comprise passing the combustion effluent out of the second fluidized bed reactor via stream 303 to a third fluidized bed reactor 250. In some embodiments, the entirety of stream 303 may be passed to the third fluidized bed reactor 250 via stream 308 (thereby eliminating the need for stream 313). In other embodiments, at least a portion of stream 303 may be passed to the third fluidized bed reactor 250 via stream 308. In further embodiments, the combustion effluent may include one or more unreacted alkanes or alkyl aromatics. In further embodiments, the combustion effluent may be passed out of the second fluidized bed reactor 220 to a separation unit via stream 303 to separate the one or more unreacted alkanes. The one or more unreacted alkanes or alkyl aromatics may be separated from a remainder of the combustion effluent using the separation unit. In some embodiments, the one or more unreacted alkanes or alkyl aromatics may then be transported out of the separation unit and passed via stream 308 to the third fluidized bed reactor 250.

The third fluidized bed reactor 250 may operate with same conditions (e.g., temperature and pressure) as was disclosed with respect to the fluidized bed reactor 110 of FIG. 1, and where the solids in third fluidized bed reactor 250 may only include the dehydrogenation catalyst. Within the third fluidized bed reactor 250, stream 308, which may comprise the combustion effluent, one or more unreacted alkanes or alkyl aromatics, or both, may be contacted with a dehydrogenation catalyst. The stream 308 may be passed into the third fluidized bed reactor and may contact the dehydrogenation catalyst in an upstream reactor section of the third fluidized bed reactor 250. Each of the chemical feed and the dehydrogenation catalyst may flow upwardly into and through the downstream reactor section of the third fluidized bed reactor 250 to produce a chemical product. The contacting of the dehydrogenation catalyst with the combustion effluent, the one or more unreacted alkanes or alkyl aromatics, or both may produce a dehydrogenated product.

In some embodiments, the dehydrogenated product and the dehydrogenation catalyst may be passed out of the downstream reactor section of the third fluidized bed reactor 250 to a separation device in a separation section within the third fluidized bed reactor 250. The dehydrogenation catalyst may be separated from the dehydrogenated product in the separation device within the third fluidized bed reactor 250. The dehydrogenated product may then be transported out of the separation section of the third fluidized bed reactor 250. For example, the separated vapors may be removed from the third fluidized bed reactor 250 via a pipe at a gas outlet port of the separation section within the third fluidized bed reactor 250. According to one or more embodiments, the separation device may be a cyclonic separation system. The cyclonic separation system may include two or more stages of cyclonic separation.

As described previously in the reactor system 100, the dehydrogenation catalyst used in the third fluidized bed reactor 250 may be slightly deactivated after contacting the one or more unreacted alkanes or alkyl aromatics. In other embodiments, the dehydrogenation catalyst may still be suitable for reaction in the third fluidized bed reactor 250. In other embodiments, a regeneration unit may remove the contaminants such as coke, raise the temperature of the dehydrogenation catalyst, or both. In some embodiments, use of a reconstituted dehydrogenation catalyst may offer renewed or regenerated activity where the deactivated dehydrogenation catalyst may exhibit reduced activity due to use, particularly where it has been used in a dehydrogenation such as is described herein, such that yield (activity) has been measurably reduced. In the case of a propane dehydrogenation, for example, the used or spent ("at least partially deactivated") dehydrogenation catalyst may be reconstituted and cycled back into the third fluidized bed reactor 250, where the dehydrogenation catalyst may exhibit a propane dehydrogenation activity that is at least 2% absolute propane conversion greater than that of the at least partially deactivated dehydrogenation catalyst under otherwise identical dehydrogenation conditions. In another embodiment the propane dehydrogenation activity exhibited by the reconstituted dehydrogenation catalyst may be greater by an amount equal to or more than 5% on the same basis.

In some embodiments, coke on the at least partially deactivated dehydrogenation catalyst may be removed by combustion in an oxygen-containing environment in the regeneration unit 230. The regeneration unit 230 may be shared with the first fluidized bed reactor 210. In some embodiments, the oxygen-containing environment may be air. In further embodiments, the dehydrogenation catalyst may be heated by additional fuel to a target temperature. The dehydrogenation catalyst may then circulate back to the first fluidized bed reactor 210, the third fluidized bed reactor 250, or both carrying the necessary heat for the dehydrogenation reaction that may take place in each respective reactor.

In additional embodiments, in one or more of the systems described as FIGS. 1-4, dehydrogenation catalyst and/or oxygen carrier material (or a dual purpose material where applicable) may be recycled within the regeneration unit. Such recycle may allow for the control of the rate of oxidation, which may improve reaction selectivity.

EXAMPLE

The following example is intended to be illustrative in nature of one or more embodiments disclosed herein. The example should not be construed as limiting in scope of the claims.

Various catalysts were tested for ethane conversion and ethylene selectivity. Table 1 shows the materials of the catalyst samples. All catalysts were made by metal impregnation.

TABLE 1

| Catalyst | Target Metals Loading (wt. %) | Support Material |
|---|---|---|
| Ga—K/ZrO$_2$ | 1.6% Ga, 0.25% K, 0.0003% Pt | Norpro ZrO$_2$ |
| Pt—Sn—K/MgAl$_2$O$_4$ | 0.6% Pt, 0.3% Sn, 0.5% Cs | Aldrich Hydrotalcite |
| Cr—K/Al$_2$O$_3$ | 1.5% Cr, 0.5% K | Siralox 1.5/70 |

The catalysts of Table 1 were tested for ethane conversion and selectivity for dehydrogenation under dry conditions and with steam, as shown in Table 2. Steam conditions tested were 10% steam. Three catalyst samples in total were tested. For each sample, a 700° C. chemical stream with a WHSV=3.7/hr at 1.4 bar total pressure was tested. Data was collected at 45 seconds after catalyst comes on-stream after an air regeneration. Samples utilized in dry conditions utilized a stream containing 70 mol. % ethane, 25 mol. % Ar, 5 mol. % He. Samples utilized in wet conditions utilized a stream containing 70 mol. % ethane, 15% Ar, 5 mol. % He, 10 mol. % steam. Samples used 500 mg of catalyst. As shown by the results of Table 2, some of the tested catalysts had good reactivity in steam conditions such as those that may be present in some embodiments of the presently described systems and methods.

TABLE 2

| Sample Number | Catalyst | Ethane Conversion under Dry conditions (%) | Ethylene Selectivity under Dry Conditions (%) | Ethane Conversion under Steam Conditions (%) | Ethylene Selectivity under Steam Conditions (%) |
|---|---|---|---|---|---|
| 1 | Ga—K/ZrO2 | 31.0 | 86.9 | 30.2 | 86.3 |
| 2 | Pt—Sn—Cs/MgAl$_2$O$_4$ | 13.9 | 94.7 | 35.2 | 84.6 |
| 3 | Cr—K/Al$_2$O$_3$ | 38.6 | 91.5 | 40.0 | 87.5 |

What is claimed is:

1. A method for dehydrogenating hydrocarbons comprising:
   passing a hydrocarbon feed comprising one or more alkanes or alkyl aromatics into a fluidized bed reactor, wherein at least 95 wt. % of the hydrocarbon feed has an atmospheric boiling point of less than or equal to 300° C.;
   contacting the hydrocarbon feed with a dehydrogenation catalyst in the fluidized bed reactor to produce a dehydrogenated product and hydrogen, wherein the hydrogen is hydrogen gas (H$_2$);
   contacting the hydrogen with an oxygen-rich oxygen carrier material in the fluidized bed reactor to combust the hydrogen and form an oxygen-diminished oxygen carrier material, wherein the oxygen-rich oxygen carrier material is reducible, wherein the oxygen carrier material exhibits Geldart A properties or Geldart B properties, and wherein the dehydrogenation catalyst and the oxygen-rich oxygen carrier material are separate particles;
   passing the oxygen-diminished oxygen carrier material and the dehydrogenation catalyst to a regeneration unit;
   oxidizing the oxygen-diminished oxygen carrier material in the regeneration unit to form the oxygen-rich oxygen carrier material; and
   passing the oxygen-rich oxygen carrier material to the fluidized bed reactor.

2. The method of claim 1, wherein the fluidized bed reactor operates at a temperature of greater than 600° C. and less than 850° C.

3. The method of claim 1, wherein the fluidized bed reactor comprises from 25 wt. % to 75 wt. % of the dehydrogenation catalyst based on the total weight of solids in the fluidized bed reactor.

4. The method of claim 1, wherein the oxygen-rich oxygen carrier material comprises from 1 wt. % to 20 wt. % releasable oxygen based on a total weight of the oxygen-rich oxygen carrier material.

5. The method of claim 1, wherein contacting the hydrogen with the oxygen-rich oxygen carrier material removes from 1 wt. % to 50 wt. % of the releasable oxygen from the oxygen-rich oxygen carrier material.

6. The method of claim 1, wherein contacting the hydrogen with the oxygen-rich oxygen carrier material combusts greater than 50% of the hydrogen.

7. The method of claim 1, further comprising partially reducing the oxygen-rich oxygen carrier material prior to contacting the hydrocarbon feed, the hydrogen, or both with the oxygen-rich oxygen carrier material in the fluidized bed reactor.

8. The method of claim 1, wherein a supplemental fuel is combusted in the regeneration unit to produce heat and increase the temperature of one or more of the oxygen-rich oxygen carrier material or the dehydrogenation catalyst.

9. The method of claim 1, wherein the regeneration unit operates at a temperature of 725° C. to 875° C.

10. The method of claim 1, wherein the regeneration unit has a temperature of at least 50° C. greater than that of the fluidized bed reactor.

11. The method of claim 1, wherein enough heat is generated during the re-oxidation of the oxygen-diminished oxygen carrier material to act as a source of heat for the reaction in the fluidized bed reactor.

12. The method of claim 1, the fluidized bed reactor operates at a temperature of from 625° C. to 770° C.

13. The method of claim 1, the fluidized bed reactor operates at a temperature of from 650° C. to 770° C.

14. The method of claim 1, wherein a flue gas is passed into the regeneration unit.

15. The method of claim 14, wherein the flue gas passed into the regeneration unit is all or a portion of the flue gas exiting the regeneration unit such that it is recycled to the regeneration unit.

16. The method of claim 15, wherein the flue gas passed into the regeneration unit is mixed with fresh air prior to being passed into the regeneration unit.

17. The method of claim 16, wherein a mixture of flue gas and fresh air passed into the regeneration unit comprises at least 25 mol % oxygen.

18. The method of claim 16, wherein a mixture of flue gas and fresh air passed into the regeneration unit comprises from 4 mol % to 25 mol % oxygen.

19. The method of claim 16, wherein a mixture of flue gas and fresh air passed into the regeneration unit comprises from 10 mol % to 21 mol % oxygen.

* * * * *